United States Patent [19]

Fahs, II

[11] Patent Number: 5,038,715
[45] Date of Patent: Aug. 13, 1991

[54] AQUACULTURE SYSTEM

[76] Inventor: Richard W. Fahs, II, 71 Overlook Dr., Danville, Pa. 17821

[21] Appl. No.: 338,032

[22] Filed: Apr. 14, 1989

[51] Int. Cl.$^5$ .................................................. A01K 61/00
[52] U.S. Cl. ........................................................ 119/3
[58] Field of Search ............................................ 119/3

[56] References Cited

U.S. PATENT DOCUMENTS

| | | | |
|---|---|---|---|
| 405,713 | 6/1889 | Lugrin et al. | 119/3 |
| 3,473,509 | 10/1969 | Miyamura | 119/3 |
| 3,495,572 | 2/1970 | Groves | 119/3 |
| 3,735,736 | 5/1973 | Yee et al. | 119/3 |
| 3,765,372 | 10/1973 | Moe, Jr. et al. | 119/3 |
| 3,773,014 | 11/1973 | Ewald, Jr. | 119/3 |
| 4,003,337 | 1/1977 | Moore | 119/3 |
| 4,038,945 | 8/1977 | Taborsky | 119/3 |
| 4,052,960 | 10/1977 | Birklecks et al. | 119/3 |
| 4,213,421 | 7/1980 | Droese et al. | 119/3 |
| 4,738,220 | 4/1988 | Ewald, Jr. | 119/3 |
| 4,913,093 | 4/1990 | Van Gorder | 119/3 |

FOREIGN PATENT DOCUMENTS

| | | | |
|---|---|---|---|
| 0131585 | 4/1960 | U.S.S.R. | 119/3 |
| 0897190 | 1/1982 | U.S.S.R. | 119/3 |
| 1110427 | 1/1983 | U.S.S.R. | 119/3 |
| 1409176 | 7/1988 | U.S.S.R. | 119/3 |
| 2016882 | 9/1979 | United Kingdom | 119/3 |
| 1555311 | 11/1979 | United Kingdom | 119/3 |

OTHER PUBLICATIONS

"Culture of Nonalmonid Freshwater Fishes", by Sticknet, pp. 140,145,181,184-187.

Primary Examiner—Robert P. Swiatek
Assistant Examiner—Todd E. Manahan
Attorney, Agent, or Firm—Panitch Schwarze Jacobs & Nadel

[57] ABSTRACT

An enclosed aquaculture system for growing fish comprises several successively interconnected container stages for holding growing fish. Each of the container stages has a size larger than the container stage preceding it, continuous interconnections between the container stages and a gate within the continuous interconnections controll the movement of the fish as the fish swim between the container stages. Fish of substantially the same size are maintained in each container stage as they are growing to prevent predatory destruction of smaller fish by larger fish and stress free transfer fo fish is provided as they swim form one container stage to another. In addition, methods for the continuous growing of fish in such an enclosed aquaculture system are disclosed.

1 Claim, 3 Drawing Sheets

AQUACULTURE SYSTEM

BACKGROUND OF THE INVENTION

1. Field of the Invention

The present invention relates to an aquaculture system for raising either fresh water fish, or salt water fish, in which growing fish of about the same size are kept together in each growth stage, and as they are moved from one growth stage to the next growth stage.

2. The Prior Art

Various kinds of shrimp-farming and/or fish-farming processes and apparatus have been proposed in the prior art; and these are described in the following documents.

| U.S. Pat. No. | Patentee | Date |
| --- | --- | --- |
| 3,473,509 | Miyamura | October 1969 |
| 3,765,372 | Moe, et al. | October 1973 |
| 4,052,960 | Birkbeck, et al. | October 1977 |
| 4,213,421 | Droese, et al. | July 1980 |
| 4,738,220 | Ewald | April 1988 |

A method for the selective breeding of trout is described in Soviet Union Published Application No. SU 1110427A, published Aug. 30, 1984.

Cannibalism has been noted in two working multi-component fresh culture systems by Van Gorder. In the Pineville site losses of striped bass where recorded to be over 80%. The Kutztown facility recorded losses of up to 65%. Both systems were intensive systems without graders; and in the Pineville system low feed rates of food were also noted which accounted for the higher loss rate over the Kutztown site.

The "Performance Capacity of Organisms, Stress and Water Quality" was a paper presented by Schreck at Aquaculture '89. In this paper were reported the results of tests on the energy drain and reduced immune response for Salmonid species during a 30 second dip netting test in a high density situation. It was noted that there was a 22% death rate due to the netting procedure.

The "Physiology Research to Net Stress in Striped Bass; Effect of Acclimation Temperature" was a paper presented by Davis and Parker at Aquaculture '89. This paper reported that up to 66% death occurred and the highest rate of loss occurred when a netting procedure under intensive circumstances occurred. Increased disease, depressed growth also occurred. The effects of the stress was evident for a period up to 48 hours after the netting. Also death did not occur instantly and was noticed during the 48 hour period after netting.

In the "Current Design Of The Fresh Culture System" by Van Gorder, netting stresses accounted for up to 20% death of striped bass when moved by net from one body of water to another. Fewer losses where noted when water and fish where moved in a bucket type container.

It is noted by Sticknet in "Culture of Nonsalmonid Freshwater Fishes" that striped bass are more excitable than other commonly cultured species and that fatal shock may occur during handling of the fish.

All of these prior art proposed aquaculture systems suffer from the following disadvantages. Fish of different species may be placed together in the same tank, or fish of the same species but of different sizes can be placed together in the same tank. This results in the larger, of a predatory fish, eating the smaller fish, thereby greatly reducing the fully grown fish available to be harvested from the fish farming system.

In the prior art systems, the fish are physically moved by net from one growing tank to another in a batch operation. This can readily result in a greatly increased incidence of disease or death for the fish, due to greatly increased stress caused to the fish and due to the removal of the fish secretion mucous layer, or "slime layer". This mucous layer covers the skin of the fish to protect it from disease.

In the prior art systems, whenever younger smaller fish are introduced into the system, there is a likelihood that if any are sickly that they may infect other healthier fish, because there is no quarantine chamber for newly arrived fish.

OBJECTS OF THE INVENTION

It is an object of the present invention to provide an aquaculture system that utilizes a continuously interconnected series of aqueous chambers, or zones, in which fish of substantially the same size can be quarantined, or permitted to grow; and then moved from one chamber, or zone, to another by swimming under stress-free conditions through a series of selectively restrictive interconnected passageway zones that create a continuous process for raising fish from fingerlings up to fully grown marketable size-fish ready to be harvested.

It is another object of the present invention to provide an aquaculture system, and process for raising fish, in which fish of the same size and species are grown together in each of several chambers and are moved together from one chamber to the next consecutive chamber wherein further growth occurs, until the fish are finally harvested, in a continuous overall stress-free environment, and wherein predacious larger fish are prevented from destroying smaller fish.

These and other further objects of the present invention will become more apparent as the description thereof proceeds.

SUMMARY OF THE INVENTION

The present invention provides an aquaculture system and fish farming process for raising fish in a continuous manner that has the following advantages. The aquaculture system reduces the stress caused to the fish by capturing and moving the fish by net or by hand. The aquaculture system reduces the occurrence of cannibalism in predacious fish by maintaining fish of about the same size and weight together in the same tank or zone of a tank while they are growing. By grading out any size differential which does occur, the same size fish are maintained in each tank or zone. Disease can be controlled because each tank is an independent zone and can function as a separate quarantine area. The aquaculture system provides for the continual raising and harvesting of both fresh water fish, or of salt water fish. Because the aquaculture system is self-contained, indoors, and recirculating, the fish are protected against outside contaminants, such as chemicals or microorganisms external to the system that would be brought into the system, or would get into the system from external sources.

Generally speaking, only three grow out chambers may be needed. If it is desired to produce larger fish, then additional grow out chambers are necessary in order to produce these larger fish without the predators eating the smaller fish.

The present invention is directed to an aquaculture system based on moving fish through a connector from one body of water to the next, wherein a first container A, received the fingerlings which fingerlings then grow to the capacity of container A; then the fish are split into containers B. Containers B can be any number of containers as long as they are at least twice the gallonage when combined as container A. This scenario can go on for containers C to Z depending on the size and weight of fish that are to be marketed. Furthermore, the fish are moved from one container to the next through a connector device where the fish will swim freely to the next chamber and are not directly handled or stressed. The aquaculture system can be constructed as multiple tanks, spider network, a pyramid, a fused tank or any configuration which will satisfy this relationship.

The present invention is also directed to an aquaculture system for growing fish comprising several interconnected container stages for holding fish of successively larger sizes, while these fish are growing;

means for interconnecting said container stages in a continuous manner; and gate means within said interconnecting means for controlling the movement of the fish as the fish swim between the stages;

whereby fish of the same size are maintained in each stage as they are growing to prevent predatory destruction of smaller fish by larger fish, and to provide for the stress free transfer of fish as they swim from one container stage to another.

The present invention is also directed to a process for the continuous growing of fish in a aquaculture system comprising providing several interconnected container zones for holding fish of successively larger sizes, while these fish are growing;

interconnecting said container zones in a continuous manner using interconnecting zones; and controlling the movement of the fish through said interconnecting zones as the fish swim between said container zones;

whereby fish of the same size are maintained in each stage as they are growing to prevent predatory destruction of smaller fish, and to provide for the stress free transfer of fish as they swim from one container zone to another.

Therefore, the present invention provides an aquaculture system for growing fish comprising a first container for initially holding fish fingerlings while the fingerlings grow to a first intermediate size and weight;

at least one second container for holding the first intermediate size fish from the first container, while said fish grow to a subsequent larger intermediate size and weight, said second container being at least about twice the volume of said first container or of any previous container;

a first interconnector means having a passageway restrictor means, for interconnecting said first container with said second container, said passageway restrictor means when closed preventing the movement of fish between said containers, and said passageway restrictor means when open permitting the movement of fish between said containers;

a final container for holding the subsequent larger intermediate size fish, while said fish grow to a final size and weight, said final container being at least about twice the volume of said previous second container; and a second interconnector means having a passageway restrictor means, for interconnecting said second container with said final container, said passageway restrictor means when closed preventing the movement of fish between said containers, and said passageway restrictor means when open permitting the movement of fish between said containers;

whereby said aquaculture system provides for the continuous regulated growth of said fish and for the continuously regulated movement of said fish from one container to another container under stress-free conditions, such that fish of the same size are maintained in the same container as they are growing, to prevent predatory destruction of some fish by other fish.

In addition, the present invention provides a process for the continuous growing of fish in an aquaculture system comprising providing a first zone for initially holding fish fingerlings while the fingerlings grow to a first intermediate size and weight;

providing at least one second zone for holding the first intermediate size fish from the first zone, while said fish grow to a subsequent larger intermediate size and weight, said second zone being at least about twice the volume of said first zone; and any additional second zone being twice the volume of the previous second zone;

interconnecting said first zone with said second zone by means of a first passageway zone;

selectively restricting the movement of said fish through said first passageway zone;

providing a final zone for holding the subsequent larger intermediate size fish, while said fish grow to a final size and weight, said final zone being at least about twice the volume of said second zone; or the last second zone if more than one second zones are used;

interconnecting said second zone with said final zone by means of a second passageway zone; and selectively restricting the movement of said fish through said second passageway zone;

whereby said aquaculture system provides for the continuously regulated growth of said fish and for the continuously regulated movement of said fish from one zone to another zone under stress-free conditions, such that fish of the same size are maintained in the same zone as they are growing, to prevent predatory destruction of some fish by other fish.

In a preferred embodiment, the aquaculture system of the present invention generally has the following relationship between the volume of the container and the flow of fish as it relates to the system, (1) the fish enter Tank A, or Zone A, (2) the fish are moved to Tank B, Section I; or Zone BI, this tank is twice the volume as Tank A, or Zone A, (3) the fish then move to Tank B, Section II; or Zone BII, this tank is twice the volume as Tank B, Section I, or Zone BI, (4) the fish then move to Tank C, or Zone C, this tank is twice the volume as Tank B, Section II, or Zone BII.

Tank volumes are related to Tank A, wherein Tank A=1, are that Tank B=6 and that Tank C=8. At should be noted that Tank B is divided into two section I and II, in which I=2 Tank A's in volume, and in which II=4 Tank A's in volume.

The present invention will now be described by reference to the following drawings, which are not to be deemed limitative of the present invention in any manner thereof.

DETAILED DESCRIPTION OF PREFERRED EMBODIMENTS

Figures 1, 2, 3:
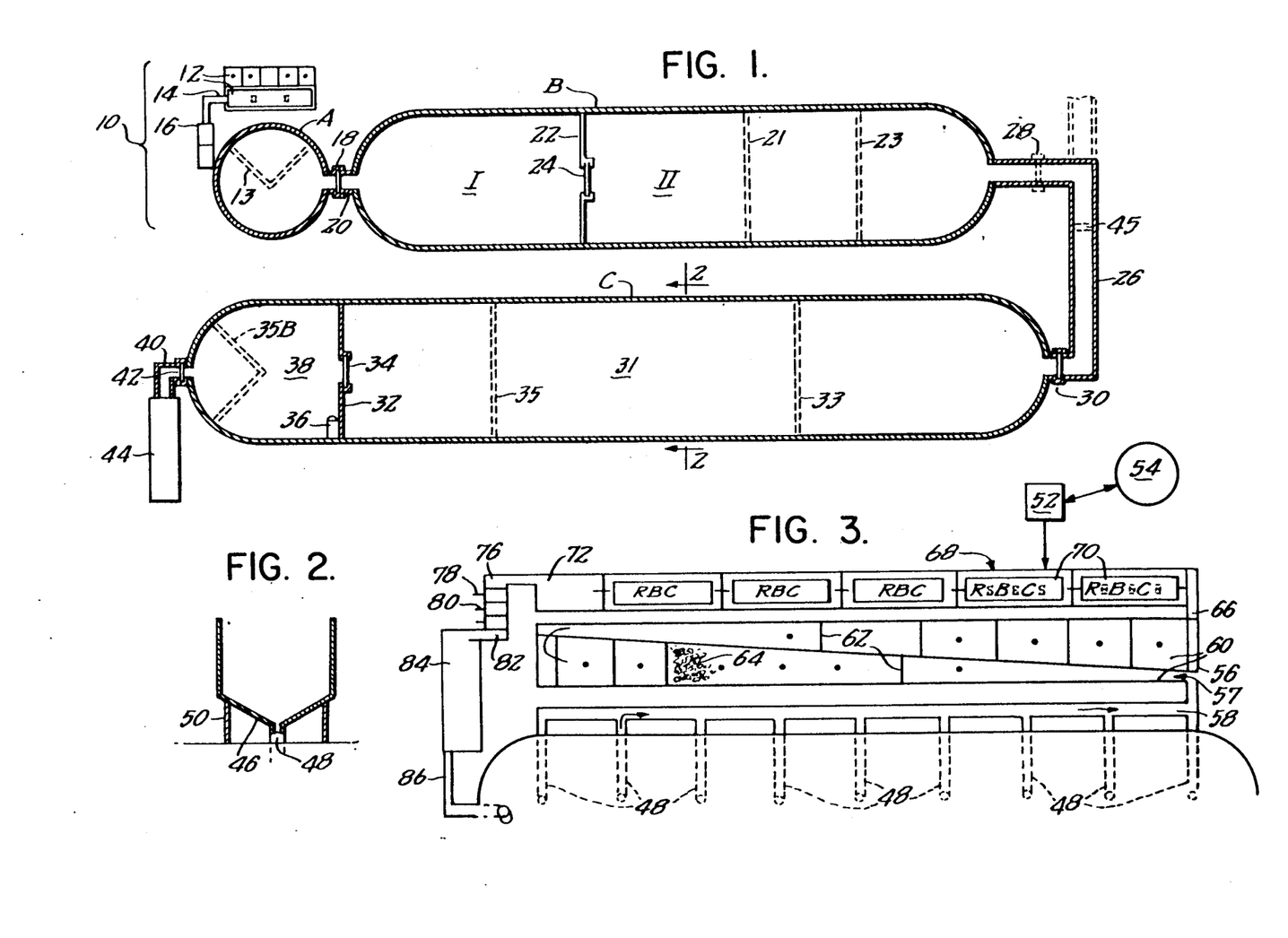
FIG. 1 is a top plan view of the interconnected holding tanks for the fish in the aquaculture system of the invention.
FIG. 2 is a partial section view of the tank B and C taken along line 2—2 of FIG. 1.
FIG. 3 is a top plan view of the clarifier and Biofiltration of the aquaculture system of the invention.

FIG. 1 illustrates a plan view of a continuous flow aquaculture system 10 for growing fish. The first container tank, or zone A, with clarifier and biofilter 12 is for holding newly arrived fingerlings. These fingerlings are checked for disease before they enter the main tanks or zones B I & II and C. There is a foam fractionator 14 and a oxygen injector 16 connected to the fingerling tank or zone A. The depth of all of the tanks and filters are usually equal and desirably are a minimum of 5 feet. Tank A is desirably 14 feet in diameter with a sloping bottom and center drain. Tank A contains grader 13. Second container, or Tank B is desirably 14 feet across and 50 feet in length, and oblong in shape. It is divided into two sections. Section I is the area where the fingerlings enter after their first 6 to 8 weeks and is twice the gallonage as tank A. The dimensions of each tank zone can vary as long as there is about twice the gallonage as a constant relationship from the previous zone to the next.

After another 6 to 8 weeks, the fish have grown to an intermediate size and are allowed to swim into Section II of tank B. Then after another 6 to 8 weeks, the fish are large enough to enter tank C for their final growth stage.

There is a grader system in each of the tanks or zones, A through C to separate the larger fish from the smaller fish. For example, in tank B Section II, there are graders 21 and 23 that can create holding pens for fish of different sizes if substantial size differentials are noticed; otherwise they are used to grade the fish in that zone. In tank C there are graders 33 and 35 that create holding pens for fish of different sizes if needed. In tank A there is a grader which is used to separation grade the fish found in tank A. Generally speaking, the grader system can desirably be a known adjustable metal bar, tube type or screen that has openings of adjustable distances that permits the smaller fish to swim through and separates out the larger fish. There can be an adjustment to the distances between the bars as the sizes of the fish varies over time. The smaller fish can readily swim through the grader system without feeling stressed, because the bars are smooth and the fish do not get stuck in the bar space openings.

There is a water tight gate or first passageway restrictor means 18 in tube or first interconnector means 20 connecting tank A to Section I of tank B. There is also a wall 22 having slide gate 24 connecting tank B, Sections I and II. Section II, tank B, is 4 times the water gallonage as tank A and 2 times the gallonage of Section I, tank B. Air lifts are used to move the water in a circular motion in all of these tanks, lifting the water from the bottom.

The air lifts can be removed easily so the graders can be moved through the section or tank or secondary interconnector means or second passageway restrictive means. A tube trough system or second interconnector means 26 has gates or second passageway restrictor means 28 and 30 and grader 45 is used to move the fish from Section II, tank B to third container tank C. The fish can be graded out at any time to be examined for problems or growth. Tank C, Section 31, is twice the gallonage as in Section II, tank B. Tank C is desirably 14 feet across, oblong in shape and is 66 feet in length. At the far end of tank C is a wall 32 and constricted funnel gate 34 system with a photo-eye counter 36 to identify the number of fish which swim into the harvest chamber 38. The harvest chamber is where the fish are held before harvesting. At the end of the chamber 38 is a harvest separator means or tube 40 and passageway restrictor means or gate 42 which leads into the harvesting trough 44, where the fish will be removed from the system. The fish are moved to the harvesting trough 44 through the tube gate by a grader, 35B. The grader at the end of the oblong can bend in the center to form a V shape to grade in the semicircle area of the Tank.

Each passageway restrictor means 18, 24, 28, 30, 34 and 42 when closed will prevent the movement of fish between the containers, and the passageway restrictor means when open will permit the movement of fish between the containers.

Figure 4:
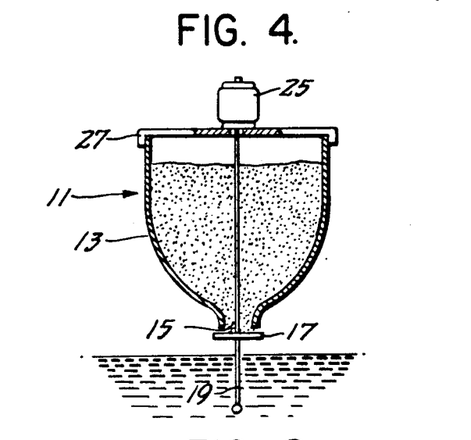
FIG. 4 is a side view of the fish feeder of the aquaculture system of the invention.
Figure 5:
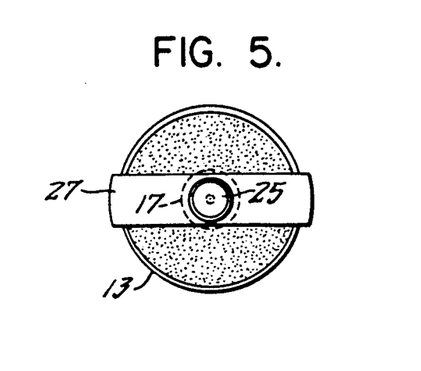
FIG. 5 is a top view of the fish feeder of FIG. 4.

The fish are feed as shown in FIGS. 4 and 5, by a combination demand/automatic feeder 11 suspended over the water by a pole hook system, which could be moved to the side of the tank when needed to be filled or moved out of the way of the grader when the grader is moved through the water. The feeder 11 is a cone shaped container 13 with a open bottom 15 where a round disk 17 larger than the opening is suspended. The feed builds up on the disk and is dispensed into the water when the longitudinal rod 19 leading through the disc is moved by the fish. The system becomes an automatic feeder when, for example, a motor 25 is attached to the top of the rod, the motor rotates the rod, dispensing feed into the water. This movement can be time controlled. The rod 19 is attached to a supporting transverse rod 27 which also supports the motor. The disk 17 can be spaced either closer to, or further from the bottom 15, so as to adjust and regulate the amount of feed to be dispensed. This unit or simular unit can currently be purchased from many commercial sources.

FIG. 2 shows a section view of tank B and C along line 2—2 of FIG. 1. Each tank has a V-shaped bottom 46 with the piping 48 under the tank so it can be easily accessed. There is a support member 50 to hold the tank above the ground or the Tank can be set in concrete or buried in the ground if plumbing access is made available. The tank can be constructed from any material which can support this weight, as long as the inside surface is a food grade approved coating (USDA Approved).

As shown in FIG. 3, a heat pump/exchanger 52 is used to both heat and/or cool the water. This unit is separate from the filtration units.

A water reservoir 54 is attached to the heat pump/exchanger 52. Water is automatically replaced at a desirable rate of 3 to 5% daily based on the water level of the system. Usually no more than 3 to 5% of the water will be exchanged in a day due to the cost of heating or cooling the reserve water.

Figure 6:
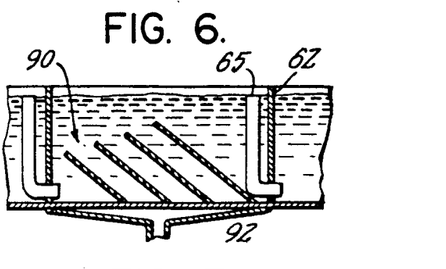
FIG. 6 is a side view of the clarifier chamber of the aquaculture system of the invention.
Figure 7:
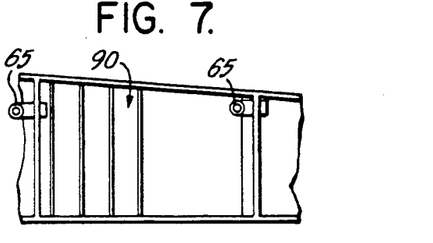
FIG. 7 is a top view of the clarifier chamber of FIG. 6.

Waste water is drawn from the bottom of the tanks and flows to the clarifier 56, as arrow 57, through piping 48 and collector tube 58. The decelerated clarifier 56 widens as the water moves down stream through it slowing the velocity of the water so that the suspended particles will fall from suspension and settle out to the bottom. The clarifiers for those tanks B and C following tank A are multiples of the basic construction to satisfy an overall clarifier length of a minimum of 100 ft. The clarifier for tank A is desirably a minimum of 36 ft. in length. The clarifier is set up to have the water move quickly at the beginning of the clarifier, then widening the water stream as it goes along downstream, therefore, slowing the water velocity and allowing the particulates to fall from suspension. In each chamber 60 the water will be collected from the top of the end of the chamber before it moves to the next chamber, over submerged barriers 62, as shown in FIGS. 6 and 7.

Each appropriate clarifier chamber 60 will be filled with floating water plants 64, which will help collect the suspended matter and will also use the nitrates which are found in the water (the end result of the nitrification process). Each clarifier chamber will repeat itself to meet the length requirements. Then the water will overflow at 66 into a long chamber 68 which will house the rotating biological contactors (RBC) 70, which are driven by air. All pumping and circulation of the water will be by air pressure unless a supplemental pump is needed. The oxygen injectors will be driven by a pump if the necessary head pressure is not reached by air lifts.

Each clarifier chamber will have a cone-shaped bottom. The above clarifier design is used as both a clarifier and plant growth chamber. Additional or separate clarification can be used if additional clarification is needed or plant growth space is limited. Such clarification can be accomplished by a low energy centrifugal clarifier or comparable unit.

Figure 8:
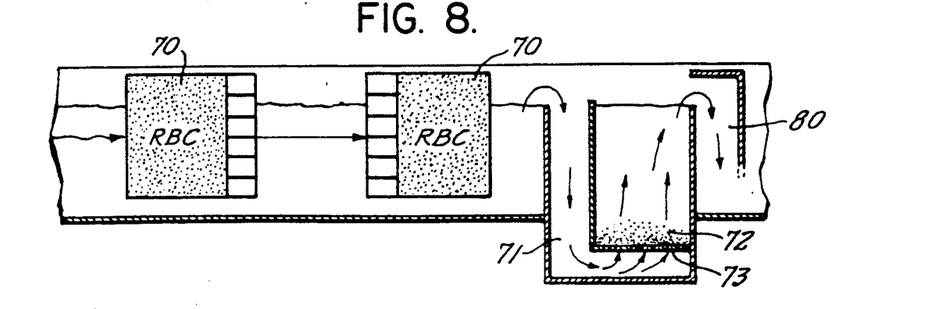
FIG. 8 is a side view of the RBC chamber of FIG. 3.

As also showing in FIG. 8, after the water moves through the RBC's 70, it will up-flow through a zeolite bed 72 to remove any nitrogen components in the water. The bed 72 may desirably be a combination of zeolite, granulated carbon and/or dolomite depending on a fresh or a salt water application. From this point, the water will move through a monitoring tank 76 where the pH of the water is tested and a buffering agent is added if needed. The water then moves through a mixing chamber 78 to the foam fractionator 80, to U.V. lights 82 and then to the oxygen injectors 84. The water is then piped back to the tanks at locations throughout the tank system through piping 86.

A computer controlled probe and monitor system will control the temperature and the oxygen levels in all of the tanks. Periodic checks of the ammonia, nitrates, carbon dioxide, total nitrogen and the nitrites are performed by use of known test kits. The nitrogen gas in the water is also tested by a known test.

All concentrated waste will move into a holding tank and then be anaerobically digested to create methane and a fixed fertilizer. The methane can be burned for heating of the room or the water. The fertilizer can be sold or used for a plant culture system to grow such plants as herbs and spices.

All pipes are arranged to provide easy access, so that they can be cleaned out periodically, if necessary.

The clarifiers as shown in FIGS. 6 and 7 are designed to accept inclined plate separators.

A back-up electrical generator and oxygen generator equipment or liquid oxygen tanks are also included in this system.

Figure 9:
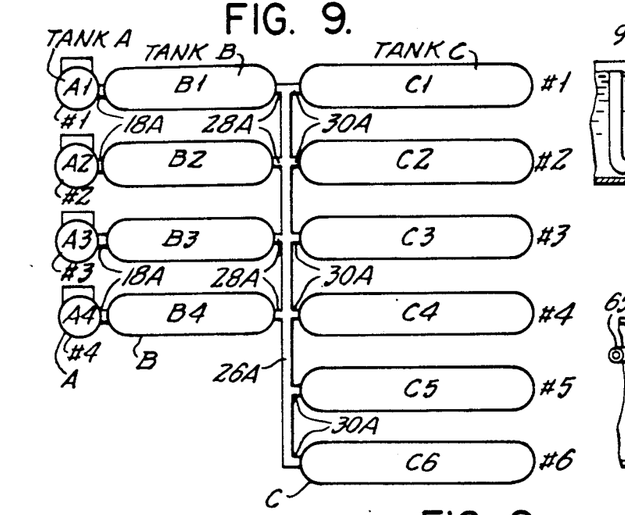
FIG. 9 is a plan view of a multitank aquaculture system of the invention.

In another embodiment, in FIG. 9, the tank C's and harvest chambers can be multiples as the tanks A and B series can be multiples. The volume relationships between tanks A, B and C are the same as for the tanks A, B and C shown in FIG. 1. Both groups are connected by a trough system 26A which allows the movement of fish from any A and B tank system to any C tank system through gates 18A, 28A and 30A. For example, there may be 4(A and B) tank systems numbered 1 through 4, and there may be 6 tank C systems numbered 1 through 6. The fish in number 1 tank A and B can be moved to any of the 6 tank C systems for final grow out. All tank systems will be able to be switched to a cool or warm species system. Yet, due to the energy involved, it is desirable to have set systems for warm or cool species. Each tank system can be any number of multiples. The "C" tank systems can be set up to be either equal in number to the "A" and "B" tank system or more numerous if larger grow out capabilities are needed. Each tank represents a complete system including the filtration units as described above, for FIGS. 1 to 8.

In the following discussion, the container stage, or the container zone, refers to that structure in the drawings, which is identified as all of the tanks labeled "A", or "B", or "C", or "D". As shown in FIGS. 1, and 9-12, each successive container stage A, B, C, and D, is larger than the preceding container stage, wherein D is larger than C which is larger than B which is larger than A. As shown in FIG. 1, each container stage has only one tank, that is in FIG. 1 there is only one tank A, or tank B, or tank C.

Figure 10:
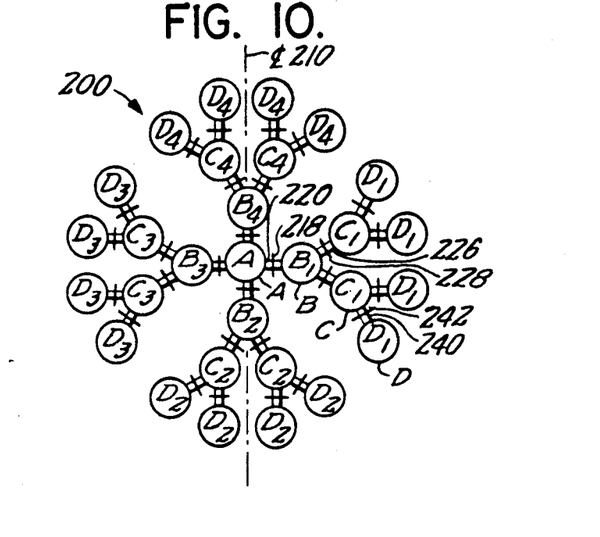
FIG. 10 is a plan view of an aquaculture system of the invention arranged as a circular cluster construction.
Figure 11:
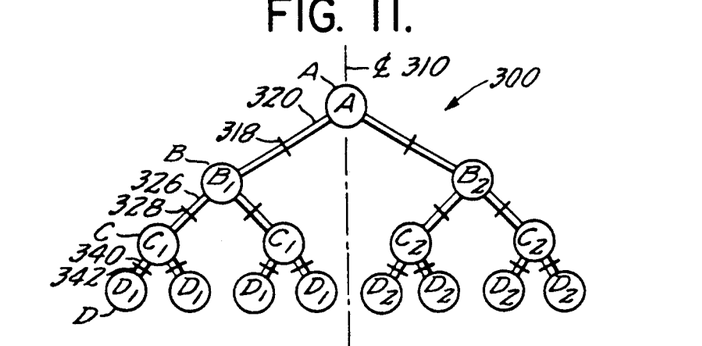
FIG. 11 is a plan view of an aquaculture system of the invention arranged as a pyramid cluster construction.
Figure 12:
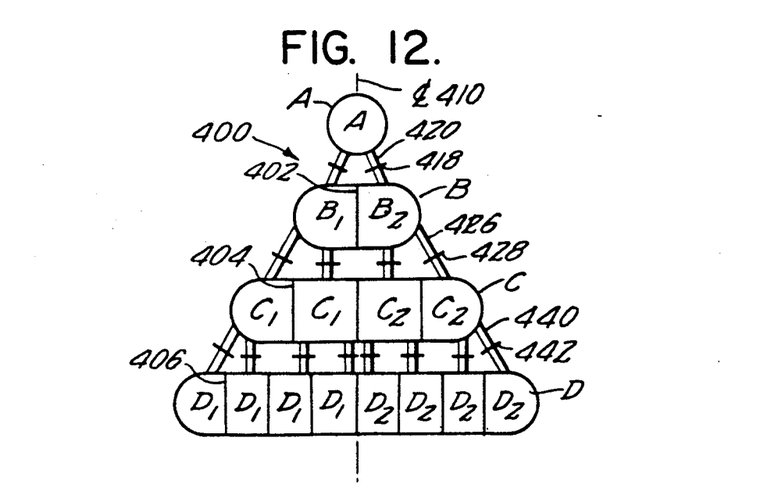
FIG. 12 is a plan view of an aquaculture system of the invention arranged as a fused pyramid construction.

In FIGS. 10, 11 and 12, the aquaculture system of the invention is such that the first container stage, or zone, has only one tank, which is tank A. In FIGS. 10, 11 and 12, each container stage, or zone, after the first container stage or zone, comprises more than one tank at each stage. Thus in FIGS. 10, 11 and 12, the second container stage, or zone, comprises more than one tank B, which is the same as subzone B. Also, there are more than one tank C, or subzone C, in the third container stage, which includes all of the tanks C. The fourth container stage, or zone includes more than one tank D, or subzone D.

As shown in FIG. 9, each container stage, or zone, comprises more than one tank, or subzone, A, B, C at each stage.

As shown in FIGS. 1 and 9-12, there are at least three interconnected successive container stages or zones, in the aquaculture system. The container at the third stage is larger than the container at the second stage; and the container at the second stage is larger than the container at the first stage. As shown in FIGS. 9-12, each container stage, or zone comprises more than one tank A, B, C or D, at each stage.

In the aquaculture system, the first container stage or zone A comprises at least one tank. In FIG. 9 it can be seen that there are four tanks within the container stage A, with each being a subzone A1, A2, A3, and A4. In FIG. 10 the aquaculture system designated 200 has only the one container stage A or zone A containing the one tank A. In FIG. 11 the aquaculture system 300 has only the one tank A in the first container stage or zone A. In FIG. 12 the aquaculture system 400 has only the one tank or container stage A which is zone A. The second interconnected container stage comprises more than one tank. In FIG. 9, which is known as the multi-tank system, the second interconnected container stage or zone B comprises the four tanks or subzones B1, B2, B3, and B4. In FIG. 10 which is known as the circular cluster system which has various stages radiating outwardly from the center tank A, there are specifically four container stages with each container stage at approximately a right angle to every other container stage grouping within the system. The second container stage or zone B contains the four tanks or subzones B1, B2, B3 and B4. These four are approximately 90° apart and arranged around central tank A. In FIG. 11 which has a cluster of container stages, specifically two container stages, arranged in a pyramidal type of construction, there are two subzones B1 and B2 within the second interconnected container stage B. In FIG. 12, which is arranged as a series of container stages in which the various subzones, such as B1 and B2 are arranged with a common wall between the subzones. In FIG. 12 the second interconnected container stage B comprises two subzones B1 and B2 having the common wall 402 between them. The third interconnected container stage comprises more than one tank. In FIG. 9 it can be seen that the third container stage or zone C comprises the six tanks or subzones C1, C2, C3, C4, C5 and C6. In FIG. 10 the third interconnected container stage or zone C comprises the subzones or tanks C1 of which there are two subzones, C2 of which there are two subzones, and C3 of which there are two subzones, and C4 of which there are two subzones. In FIG. 11 the third interconnected container stage or zone C comprises the subzones or tanks C1 of which there are two of them, and C2 of which there are two of them. In FIG. 12, the third interconnected container stage or zone C comprises the subzones or tanks C1 of which there are two of them, and C2 of which there are two of them.

In the above arrangement of the tanks container stages zones and subzones, in the third stage the total volume when combined of all the subzone tanks C is a greater total volume than the total volume when combined of all the subzone tanks B in the second stage. Also in the second stage, the total volume when combined of all the subzone tanks B is a greater total volume than the total volume when combined of all the tanks or subzones A in the first stage. However there is a proviso that any tank subzone at any given stage or zone need not be larger than a tank subzone at a preceding stage, so long as the total tank subzone volume of all of the subzone tanks at a stage is larger than the total subzone tank volume at a preceding stage.

In a preferred embodiment each successive container stage that is D, relative to C, or C relative to B, or B relative to A, is about at least twice the volume of the preceding container stage.

In aquaculture system the first interconnected container stage A has the one subzone tank A as shown in FIGS. 10, 11 and 12. The second interconnected container stage B in FIG. 10 comprises at least two subzone tanks (specifically four tanks) B1, B2, B3, and B4. In FIG. 11 the second zone B comprises at least two subzone tanks B1, and B2. In FIG. 12 zone B comprises the two subzones B1 and B2. There are interconnecting means that connect each of the two tanks of the second stage with the one tank of the first stage. In FIG. 10 the interconnecting means is 220 in FIG. 11 the interconnecting means is 320 and in FIG. 12 the interconnecting means is 420. The various interconnecting means also have a controlled means for regulating the flow of fish and movement of fish between the various tanks A and B, which are shown as gate 218 in FIG. 10, gate 318 in FIG. 11, and gate 418 in FIG. 12. The third interconnected container stage C comprises at least four subzone tanks, such as C1 having two subzones or C2 having two subzones for a total of four subzones as shown in FIG. 11 and FIG. 12. In FIG. 10 there are a total of 8 subzones in container stage C, because there are two subzones labeled C1 and two labeled C2 and two labeled C3 and two labeled C4. There are means in FIG. 10 226 for interconnecting the subzones of stage C with the subzones of stage B. There is also a gate 228 within the channel conduit 226. In FIG. 11 there is conduit 326 having gate which is a control means 328 for controlling the flow of fish or movement of fish between the tanks at zone B with the tanks at container stage C. In FIG. 12 there is channel conduit 426 having control gate 428 for regulating the flow of fish and movement of fish between the container stage B in the zone C.

The aquaculture system of FIGS. 10, 11 and 12 further comprises a fourth interconnected container stage, whereas the aquaculture system of FIG. 9 merely has the three interconnected container stages. In FIG. 10 the fourth interconnected container stage D has at least 16 subzone tanks D1, D2, D3 and D4. In FIGS. 11 and 12 there are at least 8 subzone tanks D1 and D2 with the total number of subzones being at least 8 in FIGS. 11 and 12. That is there are four D1 subzone tanks and four D2 subzone tanks. Also there are means for interconnecting these 8 subzone tanks at the fourth stage with the tanks in the third stage of zone C. In FIG. 10 the interconnecting means comprises channel conduit 240 having control gate means 242 for regulating the movement of fish between zone C and container stage zone D. In FIG. 11 the interconnecting means is channel 340 having control gate 342 that connects the subzones of stage D with the subzones of container stage C. In FIG. 12 the interconnecting means is channel conduit 440 having control gate 442 that connects container stage C with container stage zone D.

In FIG. 10, the aquaculture system comprises a tank A which is the first container stage and is located in the center of the aquaculture system along center line 210. The tanks or subzones B of the second container stage are approximately equal distantly and radially located around tank A of the first container stage. Thus tanks B1, B2, B3 and B4 are located approximately 90° apart and radially around tank A in the center. The tanks of the second container stage B are spaced from and are interconnected to the tank of the first container stage A by the interconnecting means 220. For the sake of brevity only one of the sets of container stages A, B, C, and D will be illustrated with the use of identifying numerals there in FIG. 10. In other words it can be seen that each of the interconnecting means 220 is about the same length for connecting the subzone tank B1 with tank A. The tanks or subzones C1, C2, C3, and C4 are approximately equal distantly radially located around tank A of the first container stage at a radial distance from the center tank A greater than the radial distance of the tanks and subzones B of the second container stage around the center tank A. The tanks or subzones C of the third container stage are spaced from and are interconnected to the tanks or subzones B of the second container stage by interconnecting means 226 containing gate 228. These interconnecting means 226 between subzone C1 and subzone B1 are approximately the same length and diameter. The tanks or subzone D of the fourth container stage are approximately equal distantly radially located around the tank A of the first container stage at a radial distance from the center tank A greater than the radial distance of the subzone tanks C of the third container stage around the center tank A. The tanks subzones D of the fourth container stage are spaced from and are interconnected to the tanks subzones C of the third container stage by interconnecting means 240 having gates means 242. These interconnecting means 240 are of about the same length and diameter between each set of subzones B1 and C1 as well as elsewhere around and throughout the aquaculture system 200 of FIG. 10.

The aquaculture system of FIG. 11 includes tank A of the first container stage being located along the longitudinal axis, or center line 310 of the aquaculture system. The tanks or subzones B1 and B2 of the second container stage B are adjacent to the tank of the first container stage. The arrangement of the container stages in FIG. 11 are such that the aquaculture system is constructed as a pyramid arrangement of the zones. The tanks of the second container stage B are spaced from tank A and are interconnected to tank A of the first container stage by interconnecting means 320 of the same, or of different length, and of the same, or of different, diameter. In the preferred arrangement shown in FIG. 11, the interconnecting means 320 is a tube conduit or channel which is the same length and diameter for B1 as well as for B2. The tanks or subzones C of the third container stage are adjacent to the subzone tank B of the second container stage, and are located at a distance from the first container stage A greater than the distance of the subzone tanks B of the second container stage from the first container stage A. The subzone tank C of the third container stage are spaced from, and are interconnected to the tanks subzones B of the second container stage, by interconnecting means 326 which is of a lesser length than the length of the interconnecting means 320 connecting the subzones tanks B to the tank A of the first container stage. The subzone tank D of the fourth container stage are adjacent to the subzones tanks C of the third container stage, and are located at a distance from the first container stage A greater than the distance of the subzone tanks C of the third container stage from the first container stage A. The tank D of the fourth container stage are spaced from and are interconnected tank C of the third container stage by an interconnecting means 340 of lesser length than the length of the interconnecting means 326 connecting the subzone tanks C of the third stage to the subzone tanks B of the second stage.

The aquaculture system of FIG. 12 is designated as 400 and is shaped like a triangle with a pyramid construction. The tank A of the first container stage is located along the longitude axis, or center line 410 of the aquaculture system 400. The tank subzones B1, B2 of the second container stage are also located along the longitude axis 410 of the aquaculture system and the subzone tanks of the second stage B are in contact with each other sharing a common wall 402 between this pair of adjacent tanks. The tanks of the second container stage B are spaced from and are interconnected to the tank A of the first container stage by interconnecting means 420 which comprises a tube or conduit channel and includes gate 418 for controlling the movement of fish between tank A and subzone B. The tanks or subzones C of the third container stage are located along the longitude axis 410 of the aquaculture system 400, and these subzone tanks C of the third stage are in contact with each other sharing a common wall 404 between each pair of adjacent tanks. The subzone tanks C of the third container stage are spaced from and are interconnected to the tanks B of the second container stage by interconnecting means 426 which is a conduit tube channel containing gate means 428 for regulating the movement of fish between stage C and stage B. The tanks of the third container stage C are at a distance from the first container stage A greater than the distance of the second container stage B from the first container stage A. The tanks or subzones D of the fourth container stage are located along the longitude axis 410 of the aquaculture system 400. The tanks or subzones D1 and D2 of the fourth stage are in contact with each other sharing a common wall 406 between each pair of adjacent tanks. The tanks D1 or D2 of the fourth container stage are spaced from and are interconnected to the tanks C of the third container stage by interconnecting means 440 which is a conduit tube that includes gate means 442 for controlling movement of fish between container stage zone D and container stage zone C. The tanks or subzones D of the fourth container stage are at a distance from the first container stage A which is greater than the distance of the third container stage C from the first container stage A.

The aquaculture system of the present invention has the advantage of reducing stress in the growing fish. When the fish population of any tank or zone grows to the capacity of that tank or section thereof (in approximately 6 to 8 weeks) a gateway is opened, giving access to the next section or tank zone. The water quality of each section or tank is checked to be virtually identical. The fish swim from one area to the next through the gateway with little or no stress. The fish are directed to the next area through the gateway by moving a grader toward the gateway, thus slowly encouraging the fish to move to the next area. The gateways are designed so the fish can find their way through the gate, yet it is difficult for the fish to find the return path to the chamber from which they came. Once all of the fish have moved into the new area the gateway is closed.

This procedure prevents the need to handle the fish, either by net or by hand. Either of these methods (net or hand) can remove the fish's protective outer slime layer. This layer is the fish's defense against disease. Also, movement by net can crush the fish which are on the bottom of the net, because of the weight of all the fish above the bottom layer.

A random sampling of the fish from each section is taken periodically to identify the growth and feed conversion rates of the fish in each section or tank. This is generally done during the grading process. A random sample of fish are captured and moved by use of a clear bucket, which moves fish and water. The fish can easily and gently be moved into a known volume and weight of water, all is weighed and the weight of the fish is determined by subtracting the known weight of the water and bucket from the total weight. The fish and water are then replaced back into the tank.

In a full tank situation, where hand or net capture is used, the fish are chased and stressed. The same occurs if the water in the tank is lowered. This problem of netting the fish is most evident when the fish are moved from one body of water to another which is what occurs in the prior art multiple tank batch and continuous harvest systems.

If the fish are not moved to another tank in a batch system of multiple tanks, the fish then have to be grown in the same tank into which they are stocked. This prior art method is a poor use of space and water. In these multiple tank batch harvest systems, generally due to the stress of handling the fish, disease occurs and subsequently the fish die. Death rates as high as 20% have been noted in such prior art systems per move where this form of fish handling occurs. As mentioned, the continuous movement of both water and fish reduces the stress the fish experiences during the transfer of the fish from one body of water to another yet this stress is virtually eliminated when fish are moved through a gate or lock system between tanks, according to the invention.

Another advantage of the present invention is a reduction of the occurrence of cannibalism in predacious fish. Examples of fish which are known to have tendencies toward cannibalism are striped bass, striped bass hybrids, trout, perch and salmon. Each tank is totally isolated from the next tank, therefore, different size fish are kept separate. Also constant grading within each tank or section removes those fish which grow faster, therefore, become larger than the other fish in that section or tank. Also grading is done for those fish which grow slower. The larger fish move to the next section, and the smaller fish move to the section from which they came. If the size of the fish are such that they do not fit in either of the two sections mentioned, the fish can be isolated within their current section by grading and then locking the grader screens into a position which is too small for either fish on either side of the grader to swim through.

Single tank apparatus of the prior art are not suitable to introduce small fish in with larger predacious fish. Yet a single tank apparatus is not set up for a predator species of fish, even with constant grading, unless the tanks are sectioned with many graders.

A prior art multiple tank combination with graders will soon run out of tanks to transfer the graded fish into. These prior art multiple tank batch processes can realize losses of up to 80% from cannibalism if they attempt to raise a predacious fish without graders and without intensive feeding. This is most evident during 1" to 5" early or intermediate stages of growth of the predatory fish species.

The present invention has the further advantage of disease control. Each of the tanks A, B and C are independent, and each can act, if necessary, as a quarantine area. In most cases, diseases in recirculating systems show up first, and most seriously, when the fingerlings are introduced to the system. In a single tank system of the prior art, this is, of course, devastating in that a diseased fingerling can infect the entire system.

In the present invention, the fingerlings are introduced into an isolation tank A where they are observed for disease, and can be treated before they are moved into the next tank B. The fingerlings must be tested and observed to be healthy before they are moved to the next tank. The fingerlings will have also grown to the capacity of the isolation tank A within 6 to 8 weeks. Facultative diseases can occur in any section, or tank, if the fish are stressed due to water quality failure, or due to improper handling. Bacterial and fungal disease are the most evident diseases which show up after the fingerling stage.

The present invention has the advantage that this system provides for a continual harvest of the fish. Fish in tank C or multiples of tank C are moved through a photo-eye gate 32, 34 and 36, whereby they are counted as they swim into the harvest holding chamber 38. Therefore, if a certain number of fish are needed for market, they can be moved into the harvest chamber 38 to wait movement into the harvest troughs 44. Movement through the counter gate is accomplished by a moving grader so that a selected weight fish can be harvested from tank C. The aquaculture system of the invention will desirably produce fish in tank C of weight from 1.25 lbs. to 2 lbs. Further growth can be realized by holding the stock in an additional tank C which can easily be added to the aquaculture system of the present invention.

The aquaculture system of the invention has the advantage of being indoors and therefore protected from nature. All lights will be artificial, with no natural light except over an isolated plant clarifier system. The lighting is regulated by timers and is on for a period of 14 to 16 hours a day with a summer intensity photo period. This process maximizes the fishes feeding habits and growth.

The aquaculture system of the invention is capable of raising fresh water species or salt water species of predacious fish. Examples of fresh water fish are striped bass, striped bass hybrids, salmon, trout, walleye, yellow perch and most any other similar species in which fingerlings can be made available in the future. Catfish and tilapia will also do quite well in these systems. Marine or salt water species such as the red drum, Mahi Mahi, pompono and other free swimming fin fish currently under investigation regarding fingerling production, can be raised in the present systems. The adaptation of the system to a salt water environment is accomplished by the addition of the proper salts, the elimination of the zeolite, and the substitution of granular carbon, (and dolomite, if desired). Proper pH must also be maintained. The addition of rock salt into the fresh water system is needed at levels of about 2 to 4 parts per thousand. This reduces any nitrite effects on the fishes hemoglobin and aids in disease control.

Commercial feeds currently on the market of sufficient protein levels are acceptable for feeding all of the above-mentioned fresh water fish species. A combination demand/automatic feeder is used to ensure proper feeding ratios. A high protein feed 35 to 55% with a 2 to 6% body weight feeding ratio is needed during the growth of the fish. This can vary as related to % body weight to conversion rate ratio, yet sufficient protein levels must be maintained. It is also important that the fish are given the largest crumble or pellet feed which the fish can devour. It is suggested that the largest edible food size not be exceeded when feeding the fish.

A differential in growth may occur if only some of the fish are able to feed which can result in the death of the smaller fish. The larger fish are able to eat the larger feed, but the smaller fish are unable to feed. A mixture of the two largest feeds are needed in some stages of accelerated growth. This is most evident during the early stages especially in predacious fish. Varying feeding locations are also needed to reduce the selective feeding habits of the fish.

The aquaculture system has another advantage that it is set up to grow either warm water or cool water species of fish. Desirably the temperature ranges run, for warm water species between 70 to 85 degrees Fahrenheit and for cool water species between 57 to 65 degrees Fahrenheit. Both the warm and cool water species are not grown in the same tank system due to the temperature requirement differences. It is suggested that a warm water system be set up beside a cool water system with a connecting heat pump/exchanger between the two systems so heat can be withdrawn from one system and transferred into the other.

The filtration of the system is by settling tank clarifiers 56 and rotating biological contactors 70 (RBC) additional centrigual clarification or equivalent unit can be added or substituted at 56. It is important to note that the RBC's create an acid water environment when working properly. If unchecked, this acid condition will shut down and in time kill the bacteria (Nitrosomonas and Nitrobacter) which convert the ammonia to nitrates. Thus a neutral pH of 7 should desirably be maintained in the fresh water systems. This is easily done by the addition of a buffering agent, for example sodium bicarbonate, because it will not produce an extreme pH change.

If the total ammonia level is high, and the pH is low, and the system is running at high temperatures, then an increase in the pH will cause the ammonia in the water to be converted to the more toxic form. This can easily kill the fish in the system, as is known in the prior art. Therefore, the aquaculture system monitors and controls the pH, which is of course very desirable when using a RBC.

During the initial start up phase for the system, there may exist a new tank syndrome. It will take a few weeks after the filters are seeded until they can handle a full load of ammonia which is excreted by the fish. Pure ammonia is added to the system to supplement the amount of ammonia which would be released by the fish which are to be introduced into the system. Once the fish are introduced into the system, the pH must be kept within a range of 6.5 to 6.8 to prevent any possibility of a large build up of toxic ammonia which in turn will kill the fish. This is accomplished by the addition of an acid to the water, preferable phosphoric acid. Once the pH starts to drop on its own, which indicates that the RBC is working, and a buffer must be added to return the pH up to the neutral level of about 7.0.

The RBC's are caused to rotate by air bubbling into the air wheel located at 2 or 3 locations on the RBC depending on its length. The RBC will rotate into the atmospheric air (of about 20 parts per hundred of oxygen). The oxygen needed by the bacteria is absorbed from the air instead of the water. Moving the wheel by air eliminates the use of a high horse powered electric motor for each RBC. Many high horse powered motors are not as energy efficient as a single air blower which can run the same number of RBC's. The RBC's are replicated and placed in series to meet the necessary surface area needed for the water volume which they will service.

The bacteria present receive oxygen from the air at concentrations much higher than what can be found in a submerged water environment unless pure oxygen is bubbled through the water and medium.

The RBC unlike prior art submerged filtering system do not clog. The most important fact about the RBC's, is that they are self-cleaning. The bacteria, once dead, slough off the plates and makes room for new bacteria growth, and is picked up and collected in the clarifiers. Dying bacteria in a submerged system will in time clog the system even if the system has perfectly clear water running through it.

The clarifier 56 widens as the water moves through it, thus accelerating the water in the beginning and then quickly slowing the water flow rate as the water spreads out. This allows the particulates to fall from suspension. As shown in FIGS. 6 and 7, a graduated incline plate separator can be added to the clarifier to allow for an additional collecting area for the suspended particles. The overflow from one chamber 60 to the next is from the top of the end of the previous chamber through the barrier 62 usually just below the water line as illustrated by the pipe 65. Pipe 65 could be elbow or L-shaped. Barrier 62 separates each chamber 60 and supports overflow pipe 65. Floating plants 64 which use the nitrates found in the water are located in the open areas of the clarifier. Light is supplied to stimulate the growth of these plants 64, with natural light being preferred. If this is not possible, then a low energy means of illumination can be substituted or added in a non-natural light environment. Each clarifier has many funnel shaped collectors 92 located at the bottom throughout the length of the clarifier.

The incline plate separators 90 are a baffle barrier system inserted onto the bottom of each chamber 60, and may be removed manually when needed to be cleaned. The incline plate separator 90 are tilted toward the upstream direction of the water flow. As shown in FIG. 7, the plates extend fully across the width of the chamber 60.

The length of the clarifier is important as is the retention time in the clarifier. Eighty-five percent of the particulates should be removed in 100 ft. of length. By use of this clarification system alone 100 ft. of clarifier is recommended for each tank except tank A, for tank A the clarifier length is no less than 36 ft. The waste in tanks A, B and C settles to the bottom of the funnels 46 where it is removed by means of a valve system and flows into an anaerobic digester. The waste is removed no less than two times a day. In the anaerobic digester, the waste is fixed and methane is produced. The methane is burned to create heat or hot water. The fixed waste is a good source of high nitrogen fertilizer and can be used in an attached greenhouse, or sold as a secondary product.

As shown in FIG. 8, the water exits the clarifier and then moves through the series of RBC's 70. At the end of the RBC section, the water moves from the bottom of an overflow chamber 71 up through holes 73 and through a bed of zeolite 72 and (granulated carbon, if desired). The zeolite removes the nitrogen gases and compounds found in the water. Zeolite can be recharged by placement into salt water. Therefore, zeolite has no application in a salt water marine system.

As shown in FIG. 3, the water is analyzed by probe for pH levels as it moves to a monitoring chamber 76 and to a mixing chamber 78, and a buffer is added by automatic auger, if needed. Buffering agents in granular form can also be added to the zeolite/carbon bed in the fresh water system and to the granular carbon in the salt water marine system. The water then moves to the foam fractionator 80. The foam is collected and removed and placed into an external container. The water then moves through a U.V. unit 82 which will treat the water to eliminate parasites or excess bacteria which could cause disease problems.

From here the water moves to the oxygen injector chamber 84. A supplemental pump is generally needed to increase the head pressure at this stage. The water is supersaturated to a level to maintain an 8-9 ppm level of oxygen in the production tanks. There are many conventional devices on the market which will meet this requirement. The oxygenated water is returned to the tank at the bottom of the tank at several locations 86 throughout the tank. The oxygen can be supplied by an oxygen generator or from liquid oxygen tanks from which the gas is vaporized.

A computer system regulates the temperature in the tanks by means of a thermostat and the oxygen in the tanks by means of an oxygen probe. The pH is monitored at the buffering dispensing area by probe. It is preferably if the temperature varies no more than 2 degrees from the set point, or to keep the oxygen from dropping below 8 ppm. It is desirable to have the pH vary in a range of 6.8 to 7.2 in the fresh water systems, or have the pH vary from 8.0 to 8.4 in the salt water marine systems. A pH of 7 is preferable for a fresh water system and a pH of 8.2 is preferable for a marine system.

The system of the invention is a recirculating aquaculture system. The water moves from tank to the filtration units and then returns to the tank. There is no direct external source of constant water flow through the system. The water for the system can be derived from city water supplies or from well water as long as it meets minimal water purity requirements. In either case, the water is placed into the water reservoir 54 where it is either heated or cool depending on the application. The water is also aerated to remove any chlorine found in a city water supply.

The water in the reservoir is tested before being transferred to the tank for chloramines, flourides and any chlorine which may be left in the water from the city treatment. All local water supplies must be tested for any problem contaminates, for example, high iron concentrations, sulfides or a polluted source of ground water. By having this control over the water source, it is possible to control and prevent the contamination of the fish in the system.

Any flow through system which draws its water directly from an open natural source is susceptible to the contaminates found in the water, and also faces the possibility of introducing disease into the system through the water source. The present system prevents these problems.

The aquaculture system of the invention is supplied with a back-up system in case of a failure of a critical component in the system. The oxygen content of the water is the most critical parameter of the system. There is a back-up generator in case of electrical failure. There is also a back-up blower in case the main blower fails. Bottled compressed oxygen is used in case the oxygen generator fails, or the liquid oxygen system fails, depending on the application used. If any of these situations occur, the computer sounds an alarm and calls a series of phone numbers to report the failure. Also, if the temperature or pH is out of range, an alarm is sounded and the phone numbers are called, automatically.

The tank components include the following elements. Removable air lifts are placed on the sides of the tanks to create a circular motion in the water. The tanks having the sloped bottoms 46 along with this circular motion of the water will allow the fish waste to be collected at the bottom drains 48 in the tanks. Additional air is connected to the sides of the tanks to provide an added oxygen supply to the water if needed or to help strip the $N_2$ and $CO_2$ from the water. All air lift and air supply units are removable so the graders can move along and through the water. The graders are adjustable tube type graders with an outer flexible barrier rim which slides along the tank sides and bottom. Tracks guide the graders from one end of the tank to the other. The Graders are also designed to bend at there center to run along the curved sides of the Tank's ends. There are many known types of graders which are available and can be manufactured to fit the dimensions of the tank.

The entire tank and filtration systems are insulated as is the building where the system is housed. The building can be any structure which has the floor capacity to hold the weight and one which can be insulated and blocked from natural light. The building should have a 11.5 ft. or better ceiling height for easy access for a walkway over the tanks to move the graders through the tanks from the top of the tanks. This is a benefit but not necessary. The tanks could also be buried if desired with plumbing access made available. It is also possible to add a platform beside the tank for the purpose of moving the graders and to work in the tank. One system housing tank A through tank C with filtration will fit in an area of approximately 6000 square feet.

The aquaculture system of the invention being closed and indoors has the added advantage of, therefore, being protected from the environment and polluting factors found in open systems. The system is non-polluting in contradistinction to the very high levels of pollution one would find in an open system. In open systems one can find pesticides, herbicides, PCB's and even raw sewage. Therefore, fish from these open or wild situations generally are found to have high concentrations of these pollutants. Being indoors and controlled, the aquaculture system is not affected by problems such as acid rain and temperature changes which are a problem in prior art open systems. Being recirculating, water shortages can be handled more effectively in the aquaculture system. The system under stress could go to a 99% recirculating stage for a period of time if water supplies where found to be in limited supply. The ability of the recirculating system of the invention to produce about 100,000 pounds of fish per year in approximately a 6000 sq. ft. working space also makes the system very space effective. By comparison, it would take many acres of ponds or many thousands of gallons of a natural free flowing water source to produce this annual poundage in an open system. (1 acre equals 43,560 sq. ft.).

Since from the foregoing, the construction and advantages of the invention may be readily understood, further explanation is believed to be unnecessary. However, since numerous modifications will readily occur to those skilled in the art after a consideration of the foregoing specification and accompanying drawings, it is not intended that the invention be limited to the exact construction shown and described, but all suitable modifications and equivalents may be resorted to which fall within the scope of the appended claims.

What is claimed is:

1. An enclosed aquaculture system for growing fish comprising:

at least four successively interconnected container stages for holding growing fish, each of said container stages having a size larger than a preceding container stage;

wherein a first interconnected container stage has one tank;

wherein a second interconnected container stage comprises at least two tanks with means for interconnecting each of said second container stage tanks with said first container stage tank;

wherein a third interconnected container stage comprises at least four tanks with means for interconnecting said third container stage tanks with said second container stage tanks;

wherein a fourth interconnected container stage comprises at least eight tanks with means for interconnecting said fourth container stage tanks with said third container stage tanks;

gate means within said interconnecting means for controlling the movement of said fish as said fish swim between the container stages;

wherein the tank of said first container stage is in the center of said aquaculture system;

wherein said tanks of said second container stage are positioned approximately equidistantly radially around the tank of said first container stage;

wherein said tanks of the second container stage are spaced from and are interconnected to said tank of said first container stage and said interconnecting means are of about the same length and diameter;

wherein said tanks of said third container stage are positioned approximately equidistantly radially around said tank of the first container stage at a radial distance from said center greater than the radial distance of the tanks of said second container stage from said center;

wherein said tanks of said third container stage are spaced from and interconnected to said tanks of said second container stage and said interconnecting means are of about the same length and diameter;

wherein said tanks of said fourth container stage are positioned approximately equidistantly radially around said tank of the first container stage at a radial distance from said center greater than the radial distance of said tanks of said third container stage from said center;

wherein said tanks of said fourth container stage are spaced from and interconnected to said tanks of said third container stage and said interconnecting means are of about the same length and diameter;

whereby fish of substantially the same size are maintained in each container stage as they are growing to prevent predatory destruction of smaller fish by larger fish, and to provide for the stress free transfer of fish as they swim from one container stage to another.

* * * * *